United States Patent
King et al.

(10) Patent No.: US 10,253,286 B2
(45) Date of Patent: Apr. 9, 2019

(54) SYSTEMS AND METHODS OF GENERATING ENERGY FROM SOLAR RADIATION

(71) Applicant: Combined Power LLC, La Jolla, CA (US)

(72) Inventors: John D. H. King, La Jolla, CA (US); Nicholas A. Kramer, Lakeside, CA (US); Erik E. Tang, San Diego, CA (US); Kristofer J. Olsen, San Diego, CA (US)

(73) Assignee: COMBINED POWER LLC, Lakeside, CA (US)

( * ) Notice: Subject to any disclaimer, the term of this patent is extended or adjusted under 35 U.S.C. 154(b) by 200 days.

(21) Appl. No.: 14/915,913

(22) PCT Filed: Sep. 3, 2014

(86) PCT No.: PCT/US2014/053786
§ 371 (c)(1),
(2) Date: Mar. 2, 2016

(87) PCT Pub. No.: WO2015/034862
PCT Pub. Date: Mar. 12, 2015

(65) Prior Publication Data
US 2016/0201949 A1 Jul. 14, 2016

Related U.S. Application Data

(60) Provisional application No. 61/873,714, filed on Sep. 4, 2013.

(51) Int. Cl.
*C12M 1/00* (2006.01)
*F24S 50/20* (2018.01)
(Continued)

(52) U.S. Cl.
CPC ............ *C12M 21/02* (2013.01); *C12M 23/02* (2013.01); *C12M 23/06* (2013.01); *C12M 23/26* (2013.01);
(Continued)

(58) Field of Classification Search
CPC .................... F24J 2/52; F24J 2/14; F24J 2/36
(Continued)

(56) References Cited

U.S. PATENT DOCUMENTS 3,125,091 A    3/1964  Sleeper
3,415,719 A *  12/1968 Telkes .................. B01D 5/0066
                                                    202/83

(Continued)

FOREIGN PATENT DOCUMENTS

CN    102483265 A    5/2012
CN    102889699 A    1/2013
(Continued)

OTHER PUBLICATIONS

Office Action dated Jun. 2, 2017 in related Chinese Patent Application No. 201480049103.5.
(Continued)

*Primary Examiner* — Gregory L Huson
*Assistant Examiner* — Nikhil Mashruwala
(74) *Attorney, Agent, or Firm* — Eric L. Lane; Green Patent Law

(57) ABSTRACT

A solar reflector assembly is provided for generating energy from solar radiation. The solar reflector assembly is configured to be deployed on a supporting body of liquid and to reflect solar radiation to a solar collector. The solar reflector assembly has an elongated tube having an inner portion to facilitate liquid ballast, made of semi-rigid material and a flat section built into a wall of the tube or attached to the wall of the tube. A reflective material attached to said flat section
(Continued)

of the wall of the tube to reflect solar radiation. The elongated tube has an axis of rotation oriented generally parallel to a surface of a supporting body of liquid. The elongated tube may be elastically or plastically deformed by application of a torque along its length, so as to bring flat-surface normal vectors at each end of the tube largely into alignment with each other.

18 Claims, 5 Drawing Sheets

(51) Int. Cl.
   *C12M 1/12* (2006.01)
   *F24S 30/425* (2018.01)
   *F24S 23/70* (2018.01)
   *F24S 20/70* (2018.01)
   *F24S 23/77* (2018.01)
   *F24S 25/00* (2018.01)

(52) U.S. Cl.
   CPC .......... *C12M 23/50* (2013.01); *C12M 31/02* (2013.01); *C12M 31/08* (2013.01); *F24S 20/70* (2018.05); *F24S 23/77* (2018.05); *F24S 23/82* (2018.05); *F24S 30/425* (2018.05); *F24S 50/20* (2018.05); *F24S 2023/872* (2018.05); *F24S 2025/02* (2018.05); *Y02E 10/47* (2013.01)

(58) Field of Classification Search
   USPC .............. 126/714, 626, 634, 600; 136/249
   See application file for complete search history.

(56) References Cited

U.S. PATENT DOCUMENTS

| | | | |
|---|---|---|---|
| 4,051,834 A | 10/1977 | Fletcher et al. | |
| 4,103,368 A | 8/1978 | Lockshaw | |
| 4,106,484 A | 8/1978 | Dame | |
| 4,134,392 A | 1/1979 | Livermore et al. | |
| 4,156,420 A | 5/1979 | Gunderson | |
| 4,182,307 A | 1/1980 | Brindle et al. | |
| 4,233,958 A | 11/1980 | Heden | |
| 4,239,515 A | 12/1980 | Yanagioka et al. | |
| 4,407,637 A | 10/1983 | Newby | |
| 4,473,065 A | 9/1984 | Bates | |
| 4,478,699 A | 10/1984 | Halmann et al. | |
| 4,786,795 A * | 11/1988 | Kurashima | F24J 2/38 126/573 |
| 4,874,225 A | 10/1989 | Pruszenski, Jr. | |
| 5,445,177 A | 8/1995 | Laing et al. | |
| 5,465,708 A | 11/1995 | Goebel et al. | |
| 5,650,050 A | 7/1997 | Kaufman | |
| 6,152,181 A | 11/2000 | Wapner et al. | |
| 6,223,743 B1 | 5/2001 | Prueitt | |
| 6,877,507 B2 * | 4/2005 | Braun | F24S 20/70 126/606 |
| 7,642,450 B2 | 1/2010 | Connor | |
| 7,744,555 B2 | 6/2010 | DiMauro et al. | |
| 7,980,024 B2 | 7/2011 | Berzin et al. | |
| 7,997,264 B2 | 8/2011 | Sankrithi | |
| 8,307,820 B2 | 11/2012 | King et al. | |
| 8,378,281 B2 | 2/2013 | Kats et al. | |
| 8,443,615 B2 | 5/2013 | King et al. | |
| 8,479,724 B1 | 7/2013 | Olsen | |
| 9,677,787 B2 * | 6/2017 | Tennler | F24J 2/5431 |
| 2004/0027310 A1 | 2/2004 | Braun | |
| 2004/0055594 A1 | 3/2004 | Hochberg et al. | |
| 2005/0166953 A1 | 8/2005 | Baldeschwieler | |
| 2006/0260605 A1 | 11/2006 | Connor | |
| 2007/0199560 A1 | 8/2007 | Hobbs et al. | |
| 2009/0260620 A1 | 10/2009 | Winger et al. | |
| 2009/0301547 A1 | 12/2009 | Laing | |
| 2010/0101632 A1 | 4/2010 | Kats et al. | |
| 2010/0186733 A1 | 7/2010 | Hoefler | |
| 2011/0030675 A1 | 2/2011 | King et al. | |
| 2011/0070635 A1 | 3/2011 | King et al. | |
| 2011/0113806 A1 | 5/2011 | King et al. | |
| 2012/0234668 A1 | 9/2012 | King et al. | |
| 2013/0032136 A1 | 2/2013 | King et al. | |
| 2013/0152393 A1 | 6/2013 | King et al. | |
| 2013/0306139 A1 | 11/2013 | Bostwick | |
| 2014/0208746 A1 * | 7/2014 | Yeomans | F24J 2/42 60/641.15 |
| 2014/0283815 A1 | 9/2014 | Watts | |
| 2015/0155827 A1 * | 6/2015 | Yeomans | F24J 2/14 136/246 |

FOREIGN PATENT DOCUMENTS

| | | |
|---|---|---|
| WO | WO 2008/119094 A2 | 10/2008 |
| WO | WO 2008/120943 A1 | 10/2008 |
| WO | WO 2010/132917 A1 | 11/2010 |

OTHER PUBLICATIONS

English translation of Office Action dated Jun. 2, 2017 in related Chinese Patent Application No. 201480049103.5.
Search Report with Opinion on Patentability dated Jun. 20, 2017 in related Moroccan Patent Application No. 38883.
Examination Report No. 1 dated Oct. 16, 2017 in related Australian Patent Application No. 2014315406.
Extended European Search Report dated Mar. 27, 2017 in related European Patent Application No. 14842519.2.
Examination Report dated Mar. 15, 2018 in related Australian Patent Application No. 2014315406.
Technical Report sent Jan. 10 2018 in related Omani Patent Application No. OM/P/2016/00061.
International Preliminary Report on Patentability from International Application No. PCT/US2011/052789.
International Search Report and Written Opinion from International Application No. PCT/US2011/061025.
International Search Report and Written Opinion from International Application No. PCT/US2011/052789.
International Search Report and Written Opinion from International Application No. PCT/US2010/044313.
International Search Report and Written Opinion from related International Application No. PCT/US2014/053786.
International Preliminary Report on Patentability from related International Application No. PCT/US2014/053786.
Office Action dated Aug. 8, 2018 in related Chinese Patent Application No. 201480049103.5.

\* cited by examiner

SYSTEMS AND METHODS OF GENERATING ENERGY FROM SOLAR RADIATION

CROSS-REFERENCE TO RELATED APPLICATION

This application claims priority to and benefit of U.S. patent application Ser. No. 61/873,714, filed Sep. 4, 2013, which is hereby incorporated by reference in its entirety.

FIELD OF THE DISCLOSURE

The present disclosure relates to solar energy systems.

BACKGROUND OF THE DISCLOSURE

There has been a long-standing need to provide energy generation from renewable sources. Various renewable energy sources have been pursued, such as solar energy, wind, geothermal, and biomass for biofuels as well as others.

Solar radiation has long been a prime candidate for fulfilling this need. Various approaches have been taken to achieve energy generation from solar radiation. Towards that end, much focus has been directed to creating a low cost solar energy conversion system that functions with high efficiency and requires little maintenance.

For example, solar panels formed of photovoltaic cells (solar cells) are used to transform light to electricity. Such systems have been implemented in various applications. Solar panels have been generally effective for small-scale electrical generation, such as powering small electronic, electrical generation for residential applications, and electrical generation for space-based systems. However, current solar panel technology has been ineffective for large-scale uses, such as electrical generation sufficient for municipal applications. The costs associated with such large-scale usages have been prohibitive. Current solar panels are relatively expensive and do not allow cost-effective energy storage.

Other approaches include concentrating solar radiation on solar collectors for energy generation, commonly referred to as concentrated solar power (CSP). CSP systems typically use reflective surfaces to concentrate the sun's energy from a large surface area on to a solar collector. For example, the concentrated solar energy can be used to heat a working fluid. The heated fluid is then used to power a turbine to generate electricity. Alternatively, photovoltaic cells can be used at the solar collector, eliminating the need for numerous, expensive cells. In an effort to maximize efficiency, the reflective surfaces of CSP systems can be coupled to a device that tracks the sun's movement, maintaining a focus on a receiver target throughout the day. Using this approach, the CSP system can optimize the level of solar radiation directed towards the solar collector.

Although such CSP systems are better than traditional flat-panel photovoltaic cells for large-scale applications, shortfalls exist. For example, glass and metal reflector assemblies are expensive. Further, current tracking devices used with CSP can be relatively expensive and complicated. As a result, current approaches have yet to achieve significant market penetration because of cost issues.

Biomass production, such as algae and other microorganisms, has increasingly been of interest. The potential usage of such material is found across a wide range of applications, including biofuel feedstock production, fertilizer, nutritional supplements, pollution control, and other uses.

Current approaches for biomass production include "closed-air" systems that contain biomass production within a controlled environment, limiting exposure to outside air. Examples of such systems include closed photo-bioreactor structures forming a closed container for housing a culture medium for generating biomass. Having a controlled environment helps maximize the generation of algal material by limiting exposure to invasive species as well as controlling other environmental factors that promote algal growth. Closed-air systems significantly reduce evaporation and therefore significantly reduce demands on water resources. In addition, closed-air systems facilitate the sequestration of carbon dioxide gas, which promotes algal growth, facilities compliance with environmental regulations, and according to a large number of scientists, benefits the environment generally. However, such systems can be expensive and, in many instances, cost prohibitive.

It should be appreciated that there remains a need for a system and method of generating energy from solar radiation in low-cost, large-scale manner. The present disclosure fulfills this need and others.

SUMMARY OF THE DISCLOSURE

In general terms, the present disclosure provides a solar reflector assembly useable for generating energy from solar radiation. Embodiments of the solar reflector assemblies are elongated tubes of rigid or semi-rigid material with each tube including a reflective material to reflect solar radiation to a solar collector. This structure and the materials employed provide significant cost savings for manufacture, shipping and deployment of the solar reflector assemblies. The solar reflector assembly is configured to be deployed on a supporting body of liquid. This provides both liquid ballasting capability and structural support. Beneficially, the solar reflector assemblies are inexpensive to manufacture, deploy and operate, providing a cost effective solution for energy generation.

The assembly includes an elongated tube having an inner portion which can contain ballast liquid. The elongated tube has an axis of rotation oriented generally parallel to a surface of a supporting body of liquid and a reflective material attached to a wall of the tube to reflect solar radiation towards the solar collector. The reflective material may be attached to either an interior wall or an exterior wall of the elongated tube to form a reflective surface. The fluid facilitating ballast has a top surface that is generally parallel to a surface of a supporting body of liquid.

In exemplary embodiments, the reflective material can be configured to reflect substantially all solar radiation towards the solar collector. In another exemplary embodiment, the reflective material can be configured to substantially reflect a first prescribed wavelength range towards a solar collector and to substantially transmit a second prescribed wavelength range therethrough. One end cap assembly may be coupled to the elongated tube, or a pair of end cap assemblies can be coupled to the elongated tube, in which at least one of the end cap assemblies is configured to facilitate the flow of gas and/or liquid into and out of the elongated tube.

The tube can be configured to facilitate various geometries for the reflective material to be attached to. The section of the tube whereon the reflective material is attached, can include various cross-sectional geometries, including flat, faceted, paraboloid, and other shapes.

In an exemplary embodiment, a solar reflector assembly is provided for generating energy from solar radiation. The solar reflector assembly is configured to be deployed on a supporting body of liquid and to reflect solar radiation to a solar collector. The solar reflector assembly has an elongated tube having an inner portion to facilitate liquid ballast, made of semi-rigid material and a flat section built into a wall of the tube or attached to the wall of the tube. A reflective material attached to said flat section of the wall of the tube to reflect solar radiation. The elongated tube has an axis of rotation oriented generally parallel to a surface of a supporting body of liquid. The elongated tube may be elastically or plastically deformed by application of a torque along its length, so as to bring flat-surface normal vectors at each end of the tube largely into alignment with each other.

In a detailed aspect of an exemplary embodiment, the reflective surface is formed as a hot mirror, configured to reflect IR radiation (e.g., heat reflective) while allowing visible light to pass through (e.g., visibly transparent), across wide angles of incidence. For example, the reflective sheet allows transmittance of at least 50 percent of incident energy in the wavelength band between about 400 nm and 700 nm at normal incidence. In a detailed aspect of an exemplary embodiment, the reflective sheet allows transmittance of at least 90 percent of incident energy in the wavelength band between about 400 nm and 700 nm at normal incidence.

In another detailed aspect of selected exemplary embodiments, the reflective surface can have a high percentage of reflection for substantially all incident solar IR radiation above about 700 nm or, in other embodiments, above about 750 nm. In yet other embodiments, the reflective surface can be configured to have a high percentage of reflection within a bounded range of IR wavelengths. Exemplary ranges include 700-1200 nm, 700-2000 nm, 750-1200 nm, and 750-2000 nm, among others. It should be appreciated that other ranges can be used.

Exemplary embodiments of a solar reflector assembly comprise an elongated tube having an inner portion to facilitate liquid ballast, made of semi-rigid material, a flat section built into a wall of the tube or attached to the wall of the tube, and a reflective material attached to said flat section of the wall of the tube to reflect solar radiation. The elongated tube may have an axis of rotation oriented generally parallel to a surface of a supporting body of liquid. The elongated tube may be elastically or plastically deformed by application of a torque along its length, so as to bring flat-surface normal vectors at each end of the tube largely into alignment with each other. The solar reflector assembly may further comprise one or more individual sections that are coupled together through either rigid or flexible couplings, mid-span. Liquid ballast may or may not be used in various embodiments of this invention. In exemplary embodiments, the inner portion of the tube defines a reservoir containing fluid facilitating ballast, the fluid having a top surface generally parallel to the surface of a support body of liquid.

In exemplary methods, an individual tube is brought into alignment simultaneously at each end, then fixed into position with one or more mechanical linkages and then an additional tube is similarly configured and so-on until the desired number of tubes is configured to be aimed on the target More particularly, by example and not limitation, a system for generating energy from solar radiation is provided, comprising a pool housing a supporting body of liquid and one or more solar reflector assemblies disposed on the supporting body of liquid. Each solar reflector assembly includes an inflatable elongated tube having an upper portion formed at least partially of flexible material, a lower portion formed at least partially of flexible material and an axis of rotation oriented generally parallel to a surface of the supporting body of liquid, and a reflective material attached to a wall of the tube to form a reflective surface to reflect solar radiation towards a solar collector. The reflective material may be attached to an interior wall of the elongated tube. Alternatively, the reflective material may be attached to an exterior wall of the elongated tube.

The inner portion of the elongated tube contains liquid facilitating ballast. The liquid facilitating ballast has a top surface that is generally parallel to the surface of supporting body of liquid. The system further includes a solar collector positioned to receive reflected solar radiation from the reflective sheet and may include an electrical generator assembly configured to convert the reflected solar radiation to electricity.

Embodiments of the system for generating energy from solar radiation may further comprise an electrical generator assembly operatively coupled to the solar collector to convert the reflected solar radiation to electricity. At least one end cap assembly can be coupled to an elongated tube, and a pair of end cap assemblies can be coupled to opposing ends of the one or more elongated tubes, in which at least one of the end cap assemblies is configured to facilitate the flow of gas and/or liquid into and out of the elongated tube to maintain pressure within the tube. A rotation assembly may be coupled to an elongated tube at any location on the tube. In exemplary embodiments, a rotation assembly is coupled to at least one of the end cap assemblies to induce controlled rotation of the elongated tubes to direct the reflected solar radiation to the solar collector.

In exemplary embodiments, the solar reflector assembly may comprise one or more pass-throughs coupled to the elongated tube to facilitate the flow of gas and liquid into and out of the elongated tube.

In a detailed example of an exemplary embodiment, the solar reflector assembly or system can include a rotation assembly coupled to at least one end of the elongate tube and configured to rotate the elongated tube such that the reflective sheet directs solar radiation towards the solar collector throughout the day. In another approach, the rotation assembly is coupled to at least one end of the elongated tube to induce controlled rotation of the elongated tube to direct the reflected solar radiation towards the solar collector.

In another exemplary embodiment, a plurality of elongated tubes are coupled together along longitudinal sides, forming a raft, in which a reflective surface is disposed either within or atop each tube. Alternatively, an external solar collector can be disposed in a prescribed location, spaced apart from an elongated tube or from the raft of elongated tubes to receive reflected solar radiation from the reflective sheets.

The elongated tube may further comprise a culture medium for photosynthetic biomass, thus forming a combined solar reflector and photobioreactor assembly ("CSP/PBR"). The culture medium housed in the tube can be used, e.g., to facilitate photosynthetic biomass growth, such as algal biomass. The reflective sheet may be configured to substantially reflect a first prescribed wavelength range towards a solar collector and to substantially transmit a second prescribed wavelength range therethrough to the culture medium within the elongated tube. In this manner, a portion of solar energy is directed towards the solar collector, while another portion is utilized by the culture medium, e.g., to facilitate photosynthetic biomass growth, such as algal biomass. The CSP/PBR assemblies may be disposed on a supporting body of liquid and include a solar collector positioned to receive reflected solar radiation from the reflective sheet.

To minimize cost, tubes may be made using common plastic extrusion equipment and standard polymer resins such as PVC, ABS, Acrylic and other resins. Traditional plastic extrusion equipment is not designed to hold angular twist tolerances over long lengths. Even when extreme care is taken, plastic extrusions are often not straight enough to use in concentrated solar systems because they do not produce optical accuracy sufficient for hitting a target.

In particular, in a linear Fresnel reflector (LFR) system, it is important that the individual reflector elements are straight along their lengths, so that the entire beam of light that is reflected along the entire length of the element hits the line focus target. If an extruded reflector mounting tube is twisted, it will be impossible to hit a line focus target for more than just a portion of its length.

To correct for this type of error, two separate calibration points are used. One at each end of the tube. This takes advantage of the linear nature of deformation of plastic extrusion when a torque is applied. The tube will generally twist uniformly along its length, such that if two ends are brought into calibration independently, the span between them will also be brought into calibration. Each individual element of an array of pipes can be calibrated in this way. Each pipe can be misaligned by a different amount. If each pipe is mechanically linked, for example (and not limitation), using a four-bar mechanism, the common mechanical linkage at each end will serve to keep each individual element in alignment relative to each other individual element. The two ends, with their multiply coupled individual elements, will either need to be actuated by two or more independent actuators, or alternatively, a single linear actuator, which is connected by at least one, fully rigid (for example and not limitation: metal) connector rod.

Multiple linear actuators can be used, or a single linear actuator can be used. In the case of a single linear actuator, the individual elements must be linked at each end. The ends must be linked This phenomenon holds true even when tube length is well over 10 times the diameter.

It is advantageous to use standard low cost plastic resins and extrusion equipment, but a long length, polymer pipe with reflector mounted on top can be formed in other ways as well, this invention covers a long, semi-rigid, polymer pipe, with a reflective surface mounted on top, which is field-configurable to serve as a solar reflector.

An array of such pipes can be configured to reflect a large amount of sunlight on a target and therefore concentrate the sunlight on that target, suitable for use in industrial process heat, power generation, or other applications.

For purposes of summarizing the invention and the advantages achieved over the prior art, certain advantages of the invention have been described herein. Of course, it is to be understood that not necessarily all such advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment disclosed.

BRIEF DESCRIPTION OF THE DRAWINGS

Embodiments of the present invention will now be described, by way of example only, with reference to the following drawings in which.

DETAILED DESCRIPTION

Figure 1:
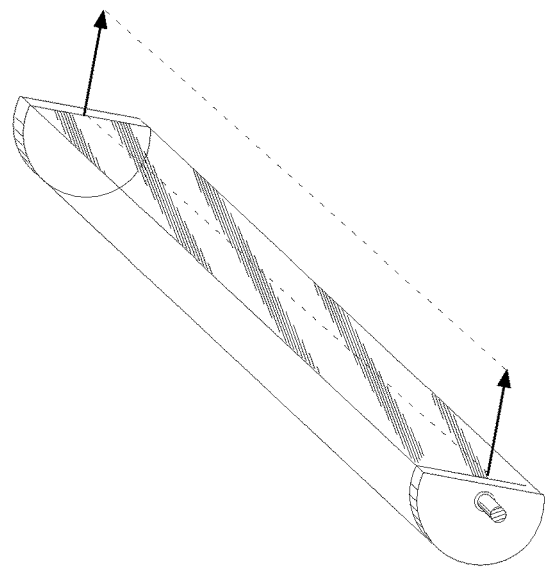
FIG. 1 is perspective view of an embodiment of a solar energy collection component in accordance with the present disclosure.

With reference now to the drawings, and particularly FIG. 1 there is shown a perspective view of a single tube with a flat section onto which a reflective material is attached. Arrows indicate a vector normal to the reflector plane at each end of the pipe. Such pipe may be rotated to reflect a beam of light that will hit a target as indicated by the dashed line between the arrow heads. This is an idealized view of a polymer pipe section that has been manufactured perfectly, and has no twist along its length.

Figure 2:
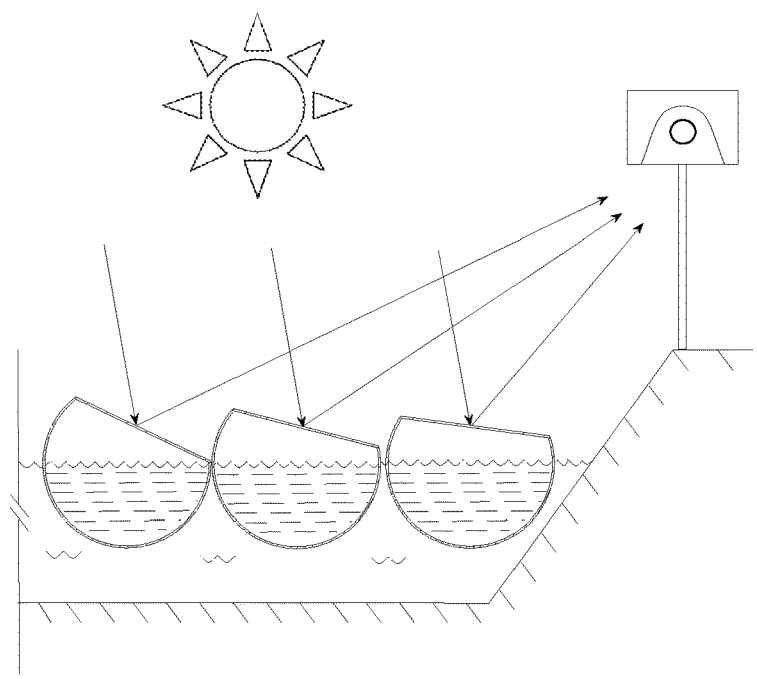
FIG. 2 is a cross sectional view of an embodiment of an array of solar reflector assemblies of a solar energy collection system in accordance with the present disclosure.

With reference now to FIG. 2, there is shown a cross section of an array of solar reflector assemblies in a constructed pool. In the idealized case from FIG. 1, the beams of light reflected by the individual tube elements will strike the target uniformly, as shown in the figure.

Figure 3:
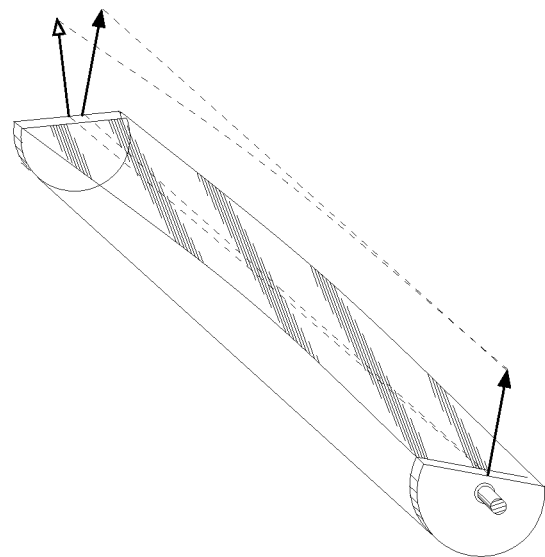
FIG. 3 is a perspective view of an embodiment of a solar energy collection component in accordance with the present disclosure.

With reference now to FIG. 3, there is shown a perspective view of a single tube with a flat section onto which a reflective material is attached. The pipe is twisted. It can be seen in the non-ideal vector normal to the actual surface at the far end, which deviates from the ideal vector normal to an idealized flat plane at the far end. The beam of light that will be reflected is shown by the curved dashed line between the two actual vectors normal. It is clear that it deviates from the straight dashed line between the first, near vector normal, and the second, idealized vector normal at the far end. This deviation, if it is anything above 1.0 degree while in use, renders such a pipe more or less useless from a solar concentration standpoint.

Figure 4:
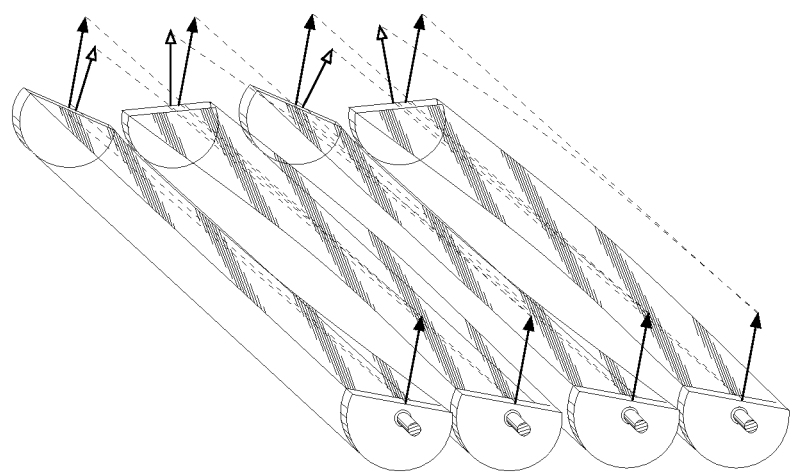
FIG. 4 is a perspective view of an embodiment of an array of solar reflector assemblies of a solar energy collection system in accordance with the present disclosure.

With reference now to FIG. 4, there is shown a perspective view of an array of solar reflector assemblies. These pipes are twisted. They are twisted in more or less random amounts and directions. The directions are shown by the white arrow heads on the ends of the vectors normal at the far ends. The beams of light reflected by the individual tube elements will strike the target uniformly at one end, the near end, but will scatter wildly at the other end, largely missing the target. This will lead to dramatically reduced performance of the solar concentrator system, rendering it more or less useless.

Figure 5:
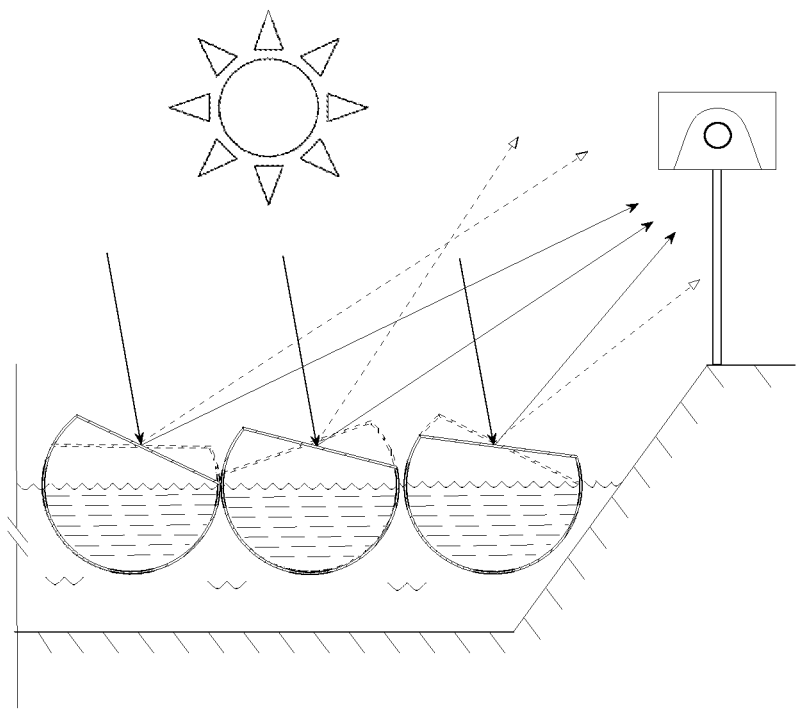
FIG. 5 is a cross sectional view of an embodiment of an array of solar reflector assemblies of a solar energy collection system in accordance with the present disclosure.

With reference now to FIG. 5, there is shown a cross sectional view of an array of solar reflector assemblies with a focus target. These pipes are twisted, as in FIG. 4. They are twisted in more or less random amounts and directions. The directions of reflected light at the near end are shown by dark arrow heads. The directions of reflected light at the far end are shown by the white arrow heads. The beams of light reflected by the individual tube elements will strike the target uniformly at one end, the near end, but will scatter wildly at the other end, largely missing the target. This will lead to dramatically reduced performance of the solar concentrator system, rendering it more or less useless.

Figure 6:
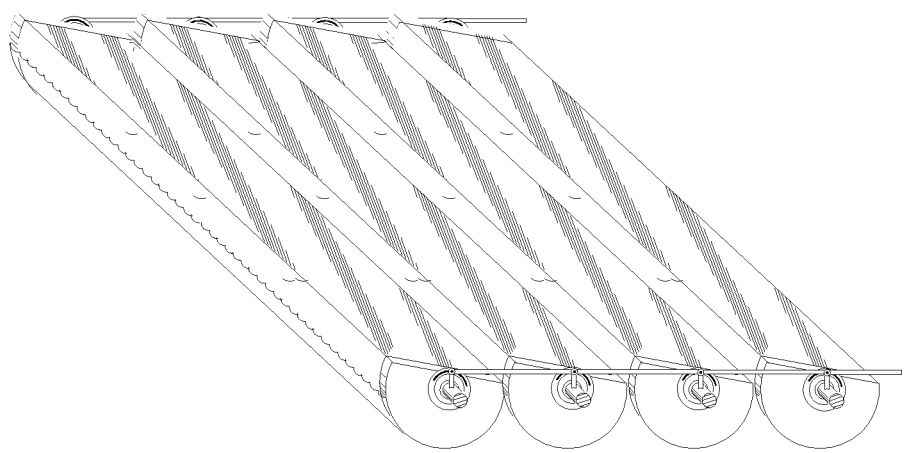
FIG. 6 is a perspective view of an embodiment of an array of solar reflector assemblies of a solar energy collection system in accordance with the present disclosure.

With reference now to FIG. 6, there is shown a perspective view of an array of solar reflector assemblies. This array is shown with a common mechanical linkage on both ends. Said mechanical linkage will suffice to allow for configuration of each individual tube element, at each end. After individual tube alignment at each end, taking advantage of the ability of semi-rigid polymer pipe to twist, the entire array is now configured to strike the target, and can be kept in focus with one or more actuators at each end, or with one actuator, and a fully rigid rod connecting the two ends.

Figure 7:
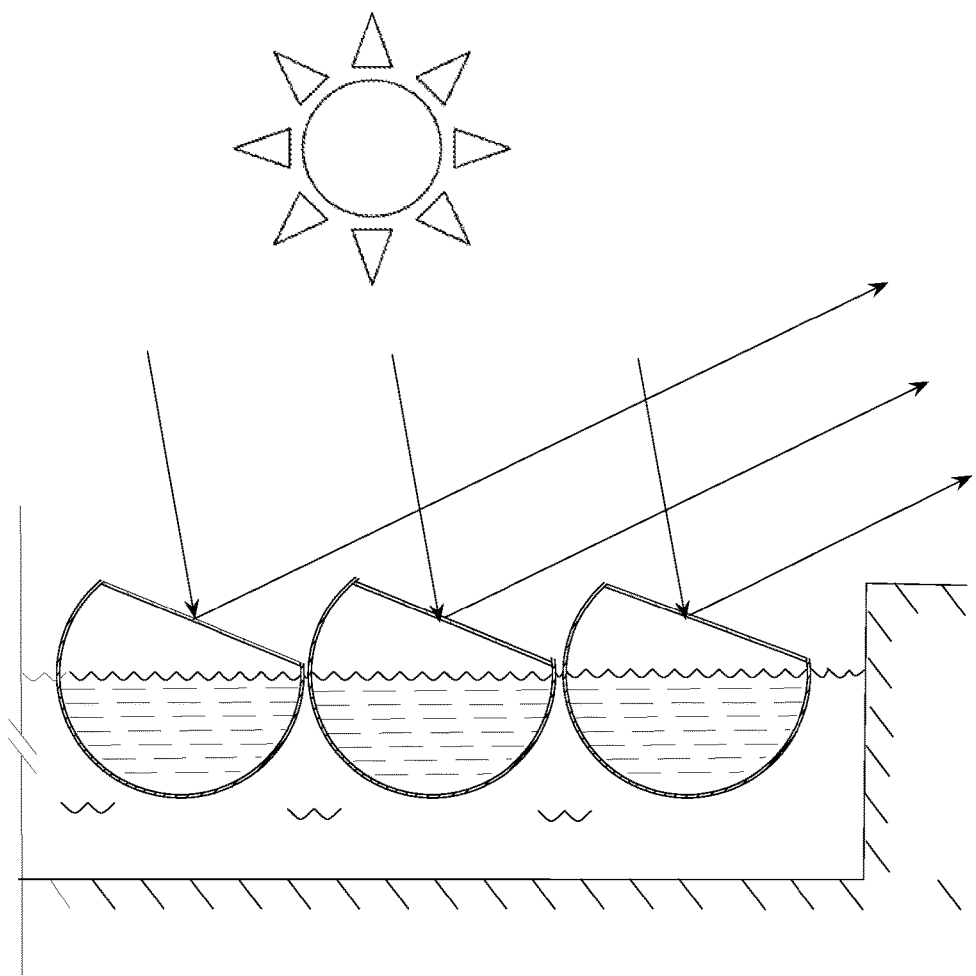
FIG. 7 is a cross sectional view of an embodiment of an array of solar reflector assemblies of a solar energy collection system in accordance with the present disclosure.

With reference now to FIG. 7, there is shown a cross section view of an array of solar reflector assemblies. Such array is configured for use in a circular pond as shown in FIG. 8.

Figure 8:
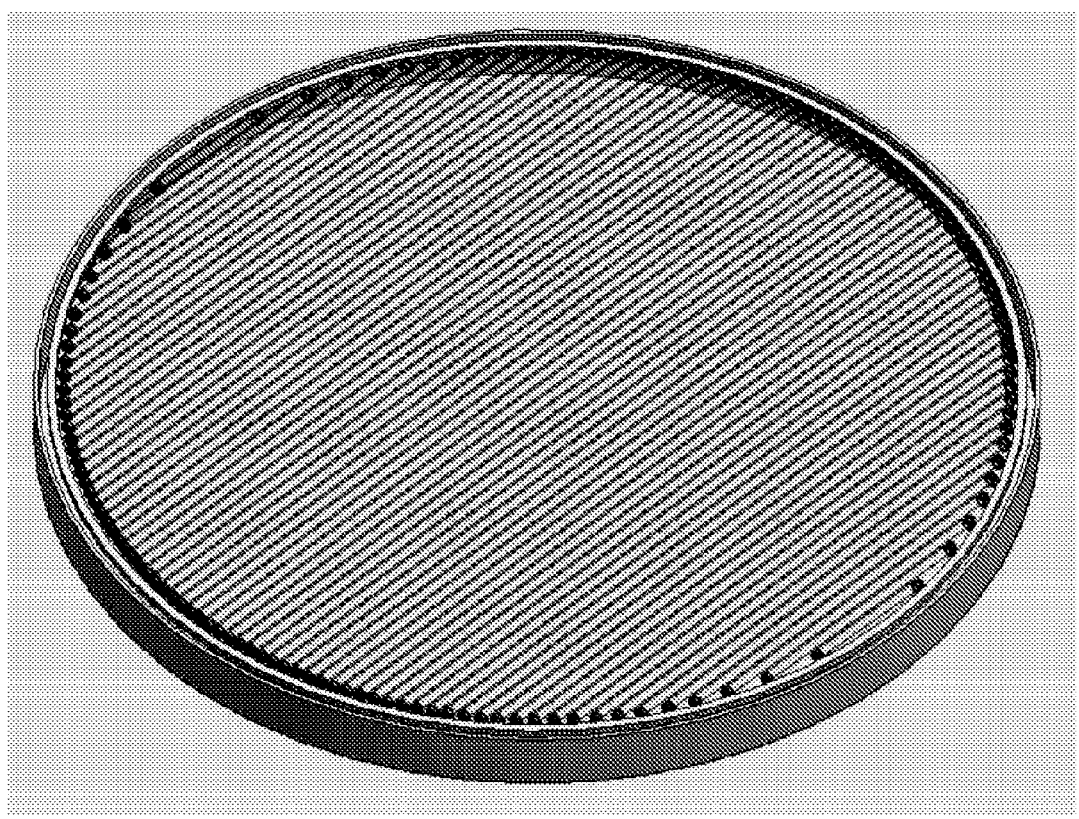
FIG. 8 is a perspective view of an embodiment of an array of solar reflector assemblies of a solar energy collection system in accordance with the present disclosure.

With reference now to FIG. 8, there is shown an array of solar reflector assemblies in a constructed pool. The entire raft of solar reflector assemblies is configured to rotate as a coherent whole about an axis of rotation generally parallel to the supporting body of liquid in the pool.

It should be noted that exemplary embodiments described herein can be controlled by a computer. Either an open loop system that is pre-programmed with the position of the sun in the sky or a closed loop system that has a sensor or sensors that detect the position of the sun in the sky or a combination of these two strategies can be used to control the position of the tubes.

Thus, it is seen that systems and methods of generating energy from solar radiation are provided. It should be understood that any of the foregoing configurations and specialized components or chemical compounds may be interchangeably used with any of the systems of the preceding embodiments. Although exemplary embodiments of the present invention are described hereinabove, it will be evident to one skilled in the art that various changes and modifications may be made therein without departing from the disclosure. It is intended in the appended claims to cover all such changes and modifications that fall within the true spirit and scope of the disclosure.

What is claimed is:

1. A solar reflector assembly comprising:
    an elongated tube having an inner portion to facilitate liquid ballast;
    a flat section built into a wall of the tube or attached to the wall of the tube;
    a reflective material attached to said flat section of the wall of the tube to reflect solar radiation; and
    a rotation assembly coupled to the elongated tube;
    wherein the elongated tube has an axis of rotation oriented generally parallel to a surface of a supporting body of liquid; and
    wherein the elongated tube twists uniformly along its length, so as to bring flat-surface normal vectors at each end of the tube largely into alignment with each other.

2. The solar reflector assembly of claim 1 further comprising an inner portion to facilitate liquid ballast, the inner portion defining a reservoir containing fluid facilitating ballast, the fluid having a top surface generally parallel to the surface of the supporting body of liquid.

3. The solar reflector assembly of claim 1 further comprising at least one end cap assembly coupled to an end of the elongated tube, the at least one end cap assembly facilitating a flow of gas and/or liquid into and out of the elongated tube.

4. The solar reflector assembly of claim 1 further comprising one or more individual sections that are coupled together through either rigid or flexible couplings.

5. The solar reflector assembly of claim 1 wherein the reflective material is attached to an interior wall of the elongated tube.

6. The solar reflector assembly of claim 1 wherein the reflective material is attached to an exterior wall of the elongated tube.

7. The solar reflector assembly of claim 1 wherein the elongated tube further comprises a culture medium for photosynthetic biomass.

8. The solar reflector assembly of claim 1 further comprising a solar collector spaced apart from the elongated tube and positioned to receive reflected solar radiation from the reflective material.

9. The solar reflector assembly of claim 1 further comprising one or more pass-throughs coupled to the elongated tube to facilitate the flow of gas and liquid into and out of the elongated tube.

10. The solar reflector assembly of claim 1 wherein the reflective sheet substantially reflects a first prescribed wavelength range and substantially transmits a second prescribed wavelength range therethrough.

11. A system for generating energy from solar radiation, comprising:
    a pool housing a supporting body of liquid;
    one or more solar reflector assemblies floating on the supporting body of liquid, each solar reflector assembly including:
    an elongated tube having an inner portion, a flat section built into a wall of the tube or attached to the wall of the tube, a reflective material attached to the flat section to reflect solar radiation;
    a rotation assembly coupled to the elongated tube;
    wherein the elongated tube has an axis of rotation oriented generally parallel to a surface of the supporting body of liquid; and
    wherein the elongated tube twists uniformly along its length, so as to bring flat-surface normal vectors at each end of the tube largely into alignment with each other;
    a solar collector spaced apart from the elongated tube and positioned to receive reflected solar radiation from the reflective sheet;
    wherein the inner portion of the elongated tube contains fluid facilitating ballast, the fluid having a top surface generally parallel to the surface of the supporting body of liquid.

12. The system of claim 11 further comprising at least one end cap assembly coupled to at least one end of the elongated tube, the at least one end cap assembly configured to facilitate the flow of liquid and/or gas into and out of the elongated tube.

13. The system of claim 11 further comprising an electrical generator assembly operatively coupled to the solar collector to convert the reflected solar radiation to electricity.

14. The system of claim 11 further comprising wherein the rotation assembly coupled to at least one of the elongated tubes to induces controlled rotation of the elongated tube to direct the reflected solar radiation towards the solar collector.

15. The system of claim 14 further comprising one or more rotation assemblies coupled to more than one tube that independently control the angle of each tube.

16. The system of claim 11 in which the pool is substantially circular, and in which the entire array of tubes can rotate about an axis of rotation oriented generally perpendicular to the supporting body of liquid.

17. The method of configuration of the system from claim 1, in which an individual tube is brought into alignment simultaneously at each end, then fixed into position with one or more mechanical linkages and then an additional tube is similarly configured and so-on until the desired number of tubes is configured to be aimed on the target.

18. A system for generating energy from solar radiation, comprising:
a pool housing a supporting body of liquid;
one or more solar reflector assemblies floating on the supporting body of liquid, each solar reflector assembly including:
an elongated tube having an inner portion, a flat section built into a wall of the tube or attached to the wall of the tube, a reflective material attached to the flat section to reflect solar radiation;
at least one end cap assembly coupled to an end of the elongated tube, the at least one end cap assembly facilitating a flow of gas and/or liquid into and out of the elongated tube;
wherein the elongated tube has an axis of rotation oriented generally parallel to a surface of the supporting body of liquid; and
a solar collector spaced apart from the elongated tube and positioned to receive reflected solar radiation from the reflective sheet;
wherein the inner portion of the elongated tube contains fluid facilitating ballast, the fluid having a top surface generally parallel to the surface of the supporting body of liquid;
wherein one or more elongated tubes twists uniformly along its length, so as to bring flat-surface normal vectors at each end of the tube largely into alignment with each other.

* * * * *